(12) United States Patent
Missel et al.

(10) Patent No.: US 6,300,069 B1
(45) Date of Patent: Oct. 9, 2001

(54) GENERATION AND AMPLIFICATION OF NUCLEIC ACIDS FROM RIBONUCLEIC ACIDS

(75) Inventors: Andreas Missel; Dirk Löffert, both of Düsseldorf; Jie Kang, Mettmann; Christian Korfhage, Langenfeld, all of (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/304,452

(22) Filed: May 3, 1999

(51) Int. Cl.[7] .............................. C12Q 1/68; C12P 19/34; C12N 9/00; C07H 21/02; C07H 21/04
(52) U.S. Cl. ............................ 435/6; 435/91.1; 435/183; 536/23.1; 536/24.33
(58) Field of Search ............................. 435/6, 91.1, 91.2, 435/91.3, 183; 536/23.1, 24.3, 24.37, 25.3

(56) References Cited

U.S. PATENT DOCUMENTS 5,580,718 * 12/1996 Resnick et al. ........................... 435/5
5,990,302 * 11/1999 Kuroita et al. ....................... 536/25.4

FOREIGN PATENT DOCUMENTS

WO-A-98 44161   10/1998   (WO) .

OTHER PUBLICATIONS

GIBCO BRL Product Catalogue and Reference Guide 1995–1996, p. 15–3.*
Chadwick et al. Comparison of three RNA amplification methods as sources of DNA for sequencing. *BioTechniques* 25(5):818–822 (Nov. 1998).
Chandler et al. Reverse transcriptase (RT) inhibition of PCR at low concentrations of template and its implications for quantitative RT–PCR. *Appl. and Environm. Microbiol.* 64(2):669–677 (Feb. 1998).
Compton, J. Nucleic acid sequence–based amplification. *Nature* 350:91–92 (1991).
Cusi et al. Comparison of M–MLV reverse transcriptase and Tth polymerase activity in RT–PCR of samples with low virus burden. *BioTechniques* 17:1034–1036 (1994).
Guatelli et al. Isothermal, in vitro amplification of nucleic acids by a multienzyme reaction modeled after retroviral replication. *PNAS USA* 87:1874–1878 (1990).
Juhasz et al. Sensitivity of tyrosinase mRNA detection by RT–PCR: rTth DNA polymerase vs. MMLV–RT and Amplitaq® polymerase. *BioTechniques* 18:678–687 (1995).
Mallet et al. Continuous RT–PCR using AMV–RT and Taq DNA polymerase: characterization and comparison to uncoupled procedures. *BioTechniques* 18:678–687 (1995).
Myers and Gelfand. Reverse transcription and DNA amplification by a *Thermus thermophilus* DNA polymerase. *Biochemistry* 30:7661–7666 (1991).
Saiki et al. Enzymatic amplification of beta–globin genomic sequences and restriction site analysis for diagnosis of sickle cell anaemia. *Science* 230:1350–1354 (1985).
Sellner and Turbett. Comparison of three RT–PCR methods. *BioTechniques* 25(2):230–234 (Aug. 1998).
Sellner et al. Reverse transcriptase inhibits Taq polymerase activity. *Nucl. Acids Res.* 20(7):1487–1490 (Apr. 11, 1992).
Sellner, et al. A one–tube, one manipulation RT–PCR reaction for detection of Ross River virus. *J. Virol. Methods* 40:255–264 (1992).
Sooknanan et al. Fidelity of nucleic acid amplification with avian myeloblastosis virus reverse transcriptase and T7 RNA polymerase. *BioTechniques* 17:1077–1085 (1994).
Xu, et al. The application of polymerase chain reaction to the detection of rotaviruses in faeces. *J. Virol. Methods* 27:29–38 (1990).
Young et al. Detection of hepatitis C virus RNA by a combined reverse transcription–polymerase chain reaction assay. *J. Clin. Microbiol.* 31:882–886 (1993).

* cited by examiner

*Primary Examiner*—Bradley L. Sisson
(74) *Attorney, Agent, or Firm*—Leon R. Yankwich; Kenneth P. Zwicker

(57) ABSTRACT

Novel compositions and methods useful for the generation of nucleic acids from a ribonucleic acid template and further nucleic acid replication are disclosed. It is shown that the generation and amplification of nucleic acids by methods that utilize two or more different polymerases, such as reverse transcriptase-polymerase chain reaction (RT-PCR), are dramatically more sensitive and efficient in the presence of a homopolymeric nucleic acid. Homopolymeric nucleic acids have been found to reduce or negate the inhibitory effect reverse transcriptases have on DNA polymerase activity. It is demonstrated that this inhibition-relieving effect of homopolymeric nucleic acids is general in nature; independent of the chemical species of homopolymer used, or the chemical composition of the polymerization reaction mixture.

45 Claims, 6 Drawing Sheets

2a
2b 5a        5b

SEQUENCE LISTING

<160> NUMBER OF SEQ ID NOS: 6

<210> SEQ ID NO 1
<211> LENGTH: 24
<212> TYPE: DNA

<213> ORGANISM: Artificial sequence
<220> FEATURE:
<221> NAME/KEY: Primer_bind
<222> LOCATION:
<223> OTHER INFORMATION: 5' primer for RANBP2

<400> SEQUENCE: 1
atgttagtga agaagaggag gatg                                              24

<210> SEQ ID NO 2
<211> LENGTH: 24
<212> TYPE: DNA
<213> ORGANISM: Artificial sequence
<220> FEATURE:
<221> NAME/KEY: Primer_bind
<222> LOCATION:
<223> OTHER INFORMATION: 3' primer for RANBP2

<400> SEQUENCE: 2
cttggcttgt agaatctgta tcaa                                              24

<210> SEQ ID NO 3
<211> LENGTH: 18
<212> TYPE: DNA
<213> ORGANISM: Artificial sequence
<220> FEATURE:
<221> NAME/KEY: Primer_bind
<222> LOCATION:
<223> OTHER INFORMATION: 5'primer for beta-actin

<400> SEQUENCE: 3
ccttgccttt gccgatcc                                                     18

<210> SEQ ID NO 4
<211> LENGTH: 23
<212> TYPE: DNA
<213> ORGANISM: Artificial sequence
<220> FEATURE:
<221> NAME/KEY: Primer_bind
<222> LOCATION:
<223> OTHER INFORMATION: 3'primer for beta-actin

<400> SEQUENCE: 4
ggatcttcat gaggtagtca gtc                                               23

<210> SEQ ID NO 5
<211> LENGTH: 21
<212> TYPE: DNA
<213> ORGANISM: Artificial sequence
<220> FEATURE:
<221> NAME/KEY: Primer_bind
<222> LOCATION:
<223> OTHER INFORMATION: 5'primer for alpha-catenin

<400> SEQUENCE: 5
agctgaaagt tgtggaagat g                                                 21

<210> SEQ ID NO 6
<211> LENGTH: 19
<212> TYPE: DNA
<213> ORGANISM: Artificial sequence
<220> FEATURE:
<221> NAME/KEY: Primer_bind -continued

```
<222> LOCATION:
<223> OTHER INFORMATION: 3'primer for alpha-catenin

<400> SEQUENCE: 6
ggagctgtct acgcaagtc                                              19
```

GENERATION AND AMPLIFICATION OF NUCLEIC ACIDS FROM RIBONUCLEIC ACIDS

FIELD OF THE INVENTION

The present invention is in the fields of molecular biology. The present invention is directed to novel compositions and methods useful for the generation of nucleic acids from a ribonucleic acid template and further nucleic acid replication. Specifically, the invention is directed to the generation and amplification of nucleic acids by reverse transcriptase-polymerase chain reaction (RT-PCR).

BACKGROUND OF THE INVENTION

The detection, analysis, transcription, and amplification of nucleic acids are the most important procedures in modern molecular biology. The application of such procedures for RNA analysis is especially important in the investigation of gene expression, diagnosis of infectious agents or genetic diseases, the generation of cDNA, and analysis of retroviruses, to name but a few applications. The reverse transcription of RNA, followed by polymerase chain reaction amplification, commonly referred to as RT-PCR or RNA-PCR, has become widely used for the detection and quantification of RNA.

The RT-PCR procedure involves two separate molecular syntheses: (i) the synthesis of cDNA from an RNA template; and (ii) the replication of the newly synthesized cDNA through PCR amplification. RT-PCR may be performed under three general protocols: (1) uncoupled RT-PCR, also referred to as two-step RT-PCR; (2) single enzyme coupled RT-PCR (coupled RT-PCR is also referred to as one-step RT-PCR or continuous RT-PCR), in which a single polymerase is used for both the cDNA generation from RNA as well as subsequent DNA amplification; and (3) two (or more) enzyme coupled RT-PCR, in which at least two separate polymerases are used for initial cDNA synthesis and subsequent replication.

In uncoupled RT-PCR, reverse transcription is performed as an independent step using buffer and reaction conditions optimal for reverse transcriptase activity. Following cDNA synthesis, an aliquot of the RT reaction product is used as template for PCR amplification with a thermostable DNA Polymerase, such as Taq DNA Polymerase, under conditions optimal for PCR amplification.

In coupled RT-PCR, reverse transcription and PCR amplification are combined into a single reaction mixture. Single enzyme RT-PCR utilizes the reverse transcriptase activity of some DNA polymerases, such as Taq DNA Polymerase and Tth DNA polymerase, whereas two-enzyme RT-PCR typically uses a retroviral or bacterial reverse transcriptase (e. g. AMV-RT, MMLV-RT, HIV-RT, EIAV-RT, RAV2-RT, Carboxydothermus hydrogenoformans DNA Polymerase or a mutant, variant or derivative thereof), and a thermostable DNA polymerase (e. g. Taq, Tbr, Tth, Tih, Tfi, Tfl, Pfu, Pwo, Kod, VENT, DEEPVENT, Tma, Tne, Bst, Pho, Sac, Sso, ES4 and others or a mutant, variant or derivative thereof).

Coupled RT-PCR provides numerous advantages over uncoupled RT-PCR. Coupled RT-PCR requires less handling of the reaction mixture reagents and nucleic acid products than uncoupled RT-PCR (e.g., opening of the reaction tube for component or enzyme addition in between the two reaction steps), and is therefore less labor intensive, reducing the required number of person hours. Coupled RT-PCR also requires less sample, and reduces the risk of contamination (Sellner and Turbett, 1998).

Single enzyme coupled RT-PCR, is the simplest RT-PCR procedure to date. This system is expensive to perform, however, due to the amount of DNA polymerase required. In addition, the single enzyme coupled RT-PCR method has been found to be less sensitive than uncoupled RT-PCR (Cusi et al., 1994), and limited to polymerizing nucleic acids of less than one kilobase pair (>1 kpb) in length. Two enzyme RT-PCR systems show increased sensitivity over the single enzyme system generally, even when coupled in a single reaction mixture. This effect has been attributed to the higher efficiency of reverse transcriptase in comparison to the reverse transcriptase activity of DNA polymerases (Sellner and Turbett, 1998).

Although the two enzyme coupled RT-PCR system is more sensitive than the uncoupled protocol, reverse transcriptase has been found to interfere directly with DNA polymerase during the replication of the cDNA, thus reducing the sensitivity and efficiency of this technique (Sellner et al., 1992; Aatsinki et al., 1994; Mallet et al., 1995). A variety of solutions to overcome the inhibitory activity of reverse transcriptase on DNA polymerase have been tried, including: increasing the amount of template RNA, increasing the ratio of DNA polymerase to reverse transcriptase, adding modifier reagents that may reduce the inhibitory effect of reverse transcriptase on DNA polymerase (e.g., non-homologous tRNA, T4 gene 32 protein, sulfur or acetate-containing molecules,), and heat-inactivation of the reverse transcriptase before the addition of DNA polymerase.

All of these modified RT-PCR methods have significant drawbacks, however. Increasing the amount of template RNA is not possible in cases where only limited amounts of sample are available. Individual optimization of the ratio of reverse transcriptase to DNA polymerase is not practicable for ready-to-use reagent kits for one-step RT-PCR. The net effect of currently proposed modifier reagents to relieve reverse transcriptase inhibition of DNA polymerization is controversial and in dispute: positive effects due to these reagents are highly dependent on RNA template amounts, RNA composition, or may require specific reverse transcriptase-DNA polymerase combinations (see, for example, Chandler et al., 1998). Finally, heat inactivation of the reverse transcriptase before the addition of the DNA polymerase negates the advantages of the coupled RT-PCR and carries with it all the disadvantages of uncouple RT-PCR systems discussed earlier.

Because of the importance of RT-PCR applications, a coupled RT-PCR system, in the form of a generalized ready-to-use composition, which exhibits high sensitivity, requires a small amount of initial sample, reduces the amount of practitioner manipulation, minimizes the risks of contamination, minimizes the expense of reagents, is not restricted to the use of specific reaction buffers, and maximizes the amount of nucleic acid end product is needed in the art.

SUMMARY OF THE INVENTION

The present invention is directed to novel compositions and methods useful for the generation of nucleic acids from a ribonucleic acid template and further nucleic acid replication. Specifically, the invention is directed to the generation and amplification of nucleic acids by reverse transcriptase-polymerase chain reaction (RT-PCR), utilizing two or more different polymerases in the presence of a homopolymeric nucleic acid. The presence of the homopolymeric nucleic acid serves to negate inhibition of the DNA polymerase, which occurs when a composition comprising two or more polymerases, at least one of which having reverse transcriptase activity, is used. The compositions and methods of present invention are used to generate and replicate DNA molecules complementary to a portion of an RNA template.

The present invention is directed generally to all reaction mixtures that can be used in the generation and replication of a nucleic acid from an RNA template. One embodiment of the present invention is directed to a composition comprising a homopolymeric nucleic acid and one or more of the following reaction components: a reverse transcriptase, a DNA polymerase, one or more oligonucleotide primers, any one or more nucleotide base, an appropriate buffering agent, a salt solution, or other additives useful in RT-PCR.

The present invention offers several advantages compared to known methods for generating cDNA from an RNA target, including, but not limited to:

permitting coupled RT-PCR, involving one reaction solution and reduced handling of reagents and products;

permitting use of a small initial sample of RNA template;

permitting use of a wide range of different reverse transcriptases;

permitting use of a wide range of different DNA polymerases;

permitting use of a wide range of different reaction mixture buffer and salt solutions, including buffers containing additional specialized reaction additives (e.g., sulfate- and acetate-containing compounds).

reducing adverse effects on the specificity and product yield (observed with tRNA additives);

operating with reagents that are commercially available, easily synthesized, and inexpensive.

The invention thus facilitates the rapid and efficient generation of nucleic acid molecules from a sample containing ribonucleic acids (RNA) as well as the detection and quantitation of RNA molecules. The invention also is useful in the rapid production and amplification of cDNAs that may be used for a variety of industrial, medical and forensic purposes.

The homopolymeric nucleic acid can be a ribonucleic acid homopolymer such as poly(A), poly(C), poly(G) or poly(U), or a deoxyribonucleic acid homopolymer such as poly(dA), poly(dC), poly(dG), poly(dT) or poly(dI). The homopolymer used for RT-PCR is an oligonucleotide of two or more bases in length, preferably between 100 to 5000 bases in length, and more preferably between 200 to 2000 bases in length. The amount of nucleic acid homopolymer used for RT-PCR may be greater than 10 ng, preferably between 10 ng to 2000 ng, more preferably between 100 ng to 1000 ng, and most preferably between 200 ng to 600 ng.

The reverse transcriptase may be any polymerase that exhibits reverse transcriptase activity. Preferably, the reverse transcriptase is AMV-RT, MMLV-RT, HIV-RT, EIAV-RT, RAV2-RT, *C. hydrogenoformans* DNA Polymerase, SUPERSCRIPT I, SUPERSCRIPT II, or mutants, variants and derivatives thereof having reverse transcriptase activity.

As used herein, mutants, variants and derivatives refer to all permutations of a chemical species, which may exist or be produced, that still retain the definitive chemical activity of that chemical species: Examples include, but are not limited to compounds that may be detectably labeled, or otherwise modified, thus altering the compound's chemical or physical characteristics.

The DNA polymerase may be any polymerase capable of replicating a DNA molecule. Preferably, the DNA polymerase is a thermostable polymerase useful in PCR. More preferably, the DNA polymerase is Taq, Tbr, Tth, Tih, Tfi, Tfl, Pfu, Pwo, Kod, VENT, DEEPVENT, Tma, Tne, Bst, Pho, Sac, Sso, Poc, Pab, ES4 or mutants, variants and derivatives thereof having DNA polymerase activity.

Oligonucleotide primers may be any oligonucleotide of two or more nucleotides in length. Primers may be random primers, homopolymers, or primers specific to a target RNA template (e.g., a sequence specific primer).

Additional compositional embodiments comprise a homopolymeric nucleic acid and other reaction mixture components such as one or more nucleotides or derivatives thereof. Preferably the nucleotide is a deoxynucleotide triphosphate: dNTP (e.g., dATP, dCTP, dGTP, dTTP, dITP, dUTP, α-thio-dNTPs, biotin-dUTP, fluorescein-dUTT, digoxigenin-dUTP).

Buffering agents, salt solutions and other additives of the present invention comprise those solutions useful in RT-PCR. Preferred buffering agents include, e.g., TRIS, TRICINE, BIS-TRICINE, HEPES, MOPS, TES, TAPS, PIPES, CAPS. Preferred salt solutions include, e.g., potassium chloride, potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate. Preferred additives include, e.g., DMSO, glycerol, formamide, betain, tetramethylammonium chloride, PEG, TWEEN 20 non-ionic surfactant, NP 40 non-ionic surfactant, ectoine, polyoles, *E. coli* SSB protein, Phage T4 gene 32 protein, BSA.

Further embodiments of this invention relate to methods for generating nucleic acids from a ribonucleic acid template and further nucleic acid replication. The method comprises: (a) adding an RNA template to a reaction mixture comprising a reverse transcriptase, a nucleic acid polymerase, or derivatives thereof, and a homopolymeric nucleic acid, and (b) incubating the reaction mixture under conditions sufficient to allow polymerization of a nucleic acid molecule complementary to at least a portion of the RNA template. In a preferred embodiment the method includes replication of the DNA molecule complementary to at least a portion of the RNA template. More preferably the method of DNA replication is polymerase chain reaction (PCR). Most preferably the method comprises coupled reverse transcriptase-polymerase chain reaction (RT-PCR).

In more specific embodiments, RT-PCR occurs between about 23° C. to about 100° C. Preferably reverse transcription occurs between about 35° C. to about 75° C., followed by PCR occurring between about 60° C. to about 95° C. Under the most preferred conditions reverse transcription occurs between about 37° C. to about 60° C., denaturation occurs at about 94° C., annealization occurs at about 60° C., and polymerization occurs at about 72° C.

BRIEF DESCRIPTION OF THE DRAWINGS

FIG. 5a depicts the RT-PCR nucleic acid products using AMPLITAQ DNA polymerase in the absence (lanes 2 through 4) of homopolymeric poly(A), and in the presence (lanes 5 through 7) of homopolymeric poly(A). Lane 1 is a nucleic acid ladder, used as a gel reference marker. FIG. 5b depicts the RT-PCR nucleic acid products using PFU DNA polymerase in the absence (lanes 2 through 4) of homopolymeric poly(A), and in the presence (lanes 5 through 7) of homopolymeric poly(A). Lanes 1 and 8 are nucleic acid ladders, used as a gel reference marker.

DETAILED DESCRIPTION OF THE INVENTION

Figure 1:
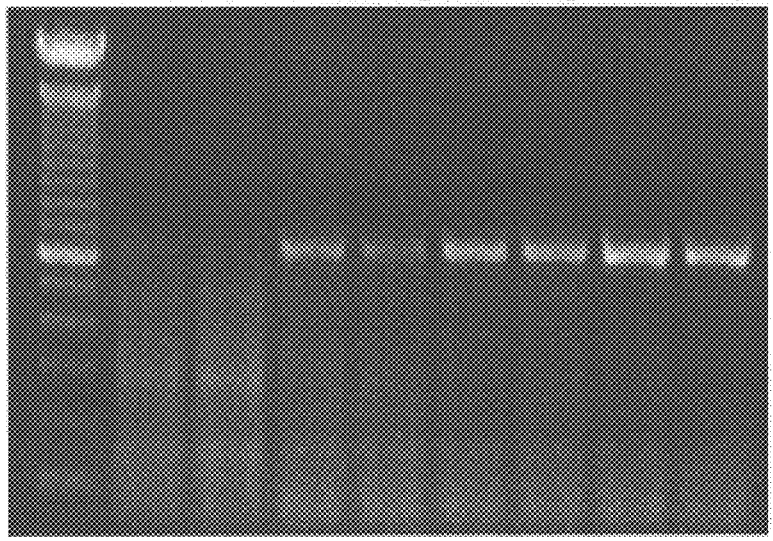
FIG. 1 is a photograph of an ethidium bromide (EtdBr)-stained 1% agarose gel, which depicts the reduction of reverse transcriptase inhibition of PCR by homopolymeric poly(A). Lane 1 is a nucleic acid ladder, used as a gel reference marker. Lanes 2 and 3 are controls, which lack homopolymeric poly(A). Lanes 4 and 5 show the nucleic acid products of an RT-PCR reaction in the presence of 100 ng of poly(A). Lanes 6 and 7 show the nucleic acid products of an RT-PCR reaction in the presence of 200 ng of poly(A). Lanes 8 and 9 show the nucleic acid products of an RT-PCR reaction in the presence of 400 ng of poly(A).

The present invention is directed to compositions and methods for use in the generation of nucleic acids from an RNA template, and particularly for reverse transcriptase-polymerase chain reaction (RT-PCR) production and analysis of nucleic acids. The invention provides compositions that include a homopolymeric nucleic acid in combination with one or more components useful in the generation of nucleic acids from an RNA template. Such components may include a reverse transcriptase, a DNA polymerase, one or more oligonucleotide primers, any one or more nucleotide bases, an appropriate buffering agent, a salt, or other additives useful in RT or RT-PCR. Methods of the invention utilize homopolymeric nucleic acid in combination with other reagents to generate nucleic acid from an RNA template, and preferably also to replicate the newly synthesized nucleic acid. The compositions and methods of the present invention useful to generate, replicate, analyze, quantitate and otherwise manipulate nucleic acid molecules are most useful in coupled or uncoupled RT-PCR procedures.

RT-PCR is one molecular manipulation used to generate and replicate a nucleic acid derived from an RNA template. RT-PCR is described herein as an exemplary protocol capable of utilizing the compositions and methods of the present invention without limitation. It is understood by one of ordinary skill in the art that the present invention has utility in other processes, which involve a combination of reverse transcriptase and DNA polymerase activity. RT-PCR involves two separate molecular syntheses: (i) the synthesis of cDNA from an RNA template; and (ii) the replication of the newly synthesized cDNA through PCR amplification.

Reverse Transcriptase-Polymerase Chain Reaction (RT-PCR)

In RT-PCR, the reaction mixture is first incubated (in an appropriate buffering agent) at a temperature sufficient to allow synthesis of a DNA molecule complementary to at least a portion of an RNA template. Components of a reverse transcription reaction mixture typically include an RNA template, from which the complementary DNA (cDNA) is transcribed; a nucleic acid polymerase that exhibits reverse transcriptase activity; and the appropriate nucleotide building blocks needed for nucleic acid synthesis. For the purposes of this invention, cDNA is defined as any DNA molecule whose nucleic acid sequence is complementary to an RNA molecule. An RNA template is defined as any RNA molecule used to provide a nucleic acid sequence from which a cDNA molecule may be synthesized. The synthesis of cDNA from an RNA template is typically accomplished by utilizing a nucleic acid polymerase that exhibits reverse transcriptase activity. For the purposes of this invention, reverse transcriptase activity refers to the ability of an enzyme to polymerize a cDNA molecule from an RNA template, and reverse transcriptase broadly refers to any enzyme possessing reverse transcriptase activity. Reverse transcription typically occurs in a temperature range from about 20° C. to about 75° C., preferably from about 35° C. to about 70° C.

After reverse transcription of an RNA template to produce a cDNA molecule, the cDNA is incubated (in an appropriate buffering agent) under conditions sufficient for replication of the cDNA molecule. The reaction mixture may be the same as that of the previous reverse transcription reaction mixture, as employed in coupled (also called continuous, or one-step) RT-PCR, or the reaction mixture may comprise an aliquot of the previous reverse transcription reaction mixture and may be further modified for nucleic acid replication, as in uncoupled (or two-step) RT-PCR. Components of a replication reaction mixture typically include a nucleic acid template (in this instance the cDNA); a nucleic acid polymerase; and the appropriate nucleotide building blocks needed for nucleic acid synthesis. Nucleic acid replication refers to the polymerization of a nucleic acid whose sequence is determined by, and complementary to, another nucleic acid. DNA replication, as used herein, is synonymous with DNA amplification. Preferably DNA amplification occurs repetitively, thus replicating both strands of the nucleic acid sequence, i.e., DNA complementary to the RNA template, and DNA whose nucleic acid sequence is substantially identical to the RNA template. Repetitive, or cyclic, DNA replication may be advantageously accomplished using a thermostable polymerase in a Polymerase Chain Reaction (PCR).

PCR is a technique well known in the art. PCR is used to amplify nucleic acids by subjecting a reaction mixture to cycles of: (i) nucleic acid denaturation, (ii) oligonucleotide primer annealization, and (iii) nucleic acid polymerization. Preferred reaction conditions for amplification comprise thermocycling, i.e., alternating the temperature of the reaction mixture to facilitate each of the steps of the PCR cycle. PCR is typically extended through multiple cycles of denaturation, annealization and replication, augmented (optionally and preferably) with an initial prolonged denaturation step and a final prolonged extension (polymerization) step. Thermocycling typically occurs within a temperature range of between about 23° C. to about 100° C., and preferably between about 37° C. to about 95° C. Nucleic acid denaturation typically occurs between about 90° C. to about 100° C., preferably about 94° C. Annealization typically occurs between about 37° C. to about 75° C. preferably about 60° C. Polymerization typically occurs between about 55° C. to about 80° C., preferably about 72° C. The number of thermocycles varies immensely, depending upon practitioner preference and the quantity of DNA product desired. Preferably, the number of PCR cycles ranges from about 5 to about 99, more preferably greater than about 20 cycles, most preferably about 40 cycles.

Template RNA

The template RNA may be any ribonucleic acid of interest, known or unknown to the practitioner. Template RNA may be artificially synthesized or isolated from natural sources. Preferably the RNA is mRNA. More preferably the RNA is biologically active or encodes a biologically active polypeptide.

Homopolymeric Nucleic Acids

The present invention relates to the discovery that homopolymeric nucleic acids serve as an inhibition-relieving agent capable of suppressing, or otherwise reducing, the inhibition of nucleic acid replication by reverse transcriptase, as observed in RT-PCR. A homopolymeric nucleic acid is any oligonucleotide of two or more bases in length composed of a single nucleotide species. Homopolymeric nucleic acids may be ribonucleic acids or deoxyribonucleic acids. Preferred homopolymeric ribonucleic acids include poly(A), poly(C), poly(G) or poly(U). Preferred homopolymeric deoxyribonucleic acids include poly(dA), poly(dC), poly(dG), poly(dT) or poly(dI). The homopolymer used for RT-PCR is an oligonucleotide of two or more bases in length, preferably between 100 to 5000 bases in length, and more preferably between 200 to 2000 bases in length. The amount of nucleic acid homopolymer used for RT-PCR may be greater than 10 ng, preferably between 10 ng to 2000 ng, more preferably between 100 ng to 1000 ng, and most preferably between 200 ng to 600 ng.

Reverse Transcriptases

Reverse transcriptases useful in the present invention may be any polymerase that exhibits reverse transcriptase activity. Preferred enzymes include those that exhibit reduced RNase H activity. Several reverse transcriptases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). Preferred reverse transcriptases include: Avian Myeloblastosis Virus reverse transcriptase (AMV-RT), Moloney Murine Leukemia Virus reverse transcriptase (MMLV-RT), Human Immunovirus reverse transcriptase (HIV-RT), EIAV-RT, RAV2-RT, *C. hydrogenoformans DNA Polymerase, rTth DNA* polymerase, SUPERSCRIPT I, SUPERSCRIPT II, and mutants, variants and derivatives thereof. It is to be understood that a variety of reverse transcriptases may be used in the present invention, including reverse transcriptases not specifically disclosed above, without departing from the scope or preferred embodiments thereof.

DNA Polymerases

DNA polymerases useful in the present invention may be any polymerase capable of replicating a DNA molecule. Preferred DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the Thermococcus genus, *Thermoplasma acidophilum* (Tac), *Thermotoga neapolitana* (Tne), *Thermotoga maritima* (Tma), and other species of the Thermotoga genus, *Pyrococcus furiosus* (Pfu), *Pyrococcus woesei* (Pwo) and other species of the Pyrococcus genus, *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Several DNA polymerases are known in the art and are commercially available (e.g., from Boehringer Mannheim Corp., Indianapolis, Ind.; Life Technologies, Inc.,Rockville, Md; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). Preferably the thermostable DNA polymerase is selected from the group of Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, and active mutants, variants and derivatives thereof. It is to be understood that a variety of DNA polymerases may be used in the present invention, including DNA polymerases not specifically disclosed above, without departing from the scope or preferred embodiments thereof.

Oligonucleotide Primers

Oligonucleotide primers useful in the present invention may be any oligonucleotide of two or more nucleotides in length. Preferably, PCR primers are about 15 to about 30 bases in length, and are not palindromic (self-complementary) or complementary to other primers that may be used in the reaction mixture. Primers may be, but are not limited to, random primers, homopolymers, or primers specific to a target RNA template (e.g., a sequence specific primer). Oligonucleotide primers are oligonucleotides used to hybridize to a region of a target nucleic acid to facilitate the polymerization of a complementary nucleic acid. In preferred RT-PCR techniques, primers serve to facilitate reverse transcription of a first nucleic acid molecule complementary to a portion of an RNA template (e.g., a cDNA molecule), and also to facilitate replication of the nucleic acid (e.g., PCR amplification of DNA). Any primer may be synthesized by a practitioner of ordinary skill in the art or may be purchased from any of a number of commercial venders (e.g., from Boehringer Mannheim Corp., Indianapolis, Ind.; New England Biolabs, Inc., Beverley, Mass.; Pharmacia LKB Biotechnology, Inc., Piscataway, N.J.). It is to be understood that a vast array of primers may be useful in the present invention, including those not specifically disclosed herein, without departing from the scope or preferred embodiments thereof.

Nucleotide Bases

Nucleotide bases useful in the present invention may be any nucleotide useful in the polymerization of a nucleic acid. Nucleotides may be naturally occurring, unusual, modified, derivative, or artificial. Nucleotides may be unlabeled, or detectably labeled by methods known in the art (e.g., using radioisotopes, vitamins, fluorescent or chemiluminescent moieties, dioxigenin). Preferably the nucleotides are deoxynucleoside triphosphates, dNTPs (e.g., dATP, dCTP, dGTP, dTTP, dITP, dUTP, $\alpha$-thio-dNITs, biotin-dUTP, fluorescein-dUTP, digoxigenin-dUTP, 7-deaza-dGTP). dNTPs are also well known in the art and are commercially available venders (e.g., from Boehringer Mannheim Corp., Indianapolis, Ind.; New England Biolabs, Inc., Beverley, Mass.; Pharmacia LKB Biotechnology, Inc., Piscataway, N.J.).

Buffering Agents and Salt Solutions

Buffering agents and salts useful in the present invention provide appropriate stable pH and ionic conditions for nucleic acid synthesis, e.g., for reverse transcriptase and DNA polymerase activity. A wide variety of buffers and salt solutions and modified buffers are known in the art that may be useful in the present invention, including agents not specifically disclosed herein. Preferred buffering agents include, but are not limited to, TRIS, TRICINE, BIS-TRICINE, HEPES, MOPS, TES, TAPS, PIPES, CAPS. Preferred salt solutions include, but are not limited to solutions of; potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

Other Additives Useful in RT-PCR

Other additives capable of facilitating reverse transcription, replication, and/or a combination of both reactions (e.g., agents for facilitating RT-PCR), other than those disclosed for the first time by this invention, are known in the art. In accordance with the compositions and methods of this invention, one or more of these additives may be incorporated in the present compositions to optimize the generation and replication of nucleic acids from a ribonucleic acid template. Additives may be organic or inorganic compounds. Inhibition-relieving agents useful in the present invention include, but are not limited to, polypeptides such as; human serum albumin, bovine serum albumin (BSA), ovalbumin, albumax, casein, gelatin, collagen, globulin, lysozyme, transferrin, myoglobin, hemoglobin, $\alpha$-lactalbumin, fumarase, glyceraldehyde-3-phosphate dehydrogenase (GAPDH), amyloglucosidase, carbonic anhydrase, $\beta$-lactoglobulin, aprotinin, soybean trypsin inhibitor, trypsinogen, phosphorylase b, myosin, actin, $\beta$-galactosidase, catalase, tryptic soy digests, tryptose, lectins, *E. coli* single-stranded binding (SSB) protein, phage T4 gene 32 protein, and the like, or fragments or derivatives thereof. Examples of nonpolypeptide additives include, but are not limited to; tRNA, rRNA, sulfur-containing compounds, acetate-containing compounds, dimethylsulfoxide (DMSO), glycerol, formamide, betain, tetramethylammonium chloride (TMAC), polyethylene glycol (PEG), TWEEN 20 non-ionic surfactant, NP 40, non-ionic surfactant, ectoine, and polyols. Preferred additives include DMSO, glycerol, formamide, betain, TMAC, PEG, TWEEN 20 non-ionic surfactant, NP 40 non-ionic surfactant, ectoine, polyols, *E. coli* (SSB) protein, Phage T4 gene 32 protein, BSA.

It will be readily apparent to one of ordinary skill in the art that other suitable modifications and adaptations of the compositions and methods of the invention described herein are obvious and may be made without departing from the scope of the invention or the disclosed embodiments thereof. Having now described the present invention in detail, the same will be more clearly understood by reference to the following examples, which are included herewith for purposes of illustration only and are not intended to be limiting of the invention.

EXAMPLE 1

Inhibition of Nucleic Acid Amplification by Reverse Transcriptase

To study the inhibiting effect of reverse transcriptases on nucleic acid replication, $10^3$ and $10^2$ copies of a plasmid containing a 500 bp fragment of the RanBP2 gene were used as template for PCR amplification. The reactions were performed in a final volume of 50 $\mu$l. The reaction mixture comprised 50 mM KCl, 10 mM Tris-HCl, pH 8.3, 0.001% gelatine, 1.5 mM MgCl$_2$, 2 mM DTT, 200 $\mu$M of each dNTP, 0.16 $\mu$M sense and antisense primers (SEQ ID NOs: 1 and 2, respectively), 2.5 Units HOTSTARTAQ™ DNA polymerase (QIAGEN), 10 Units of recombinant RNASIN (PROMEGA™) and increasing amounts OMNISCRIPT RT (QIAGEN) from 0 to 5 units. To simulate a coupled RT-PCR, the PCR was preceded by an incubation step for 30 minutes at 37° C. ("pseudo RT"). The PCR program consisted of an initial RT denaturation/HOTSTARTAQ activation step (15 min, 95° C.), 45 cycles (30 sec, 94° C.; 1 min, 60° C., 1 min, 72° C.) and a final extension step (10 min, 72°C. PCR was performed in a BIOMETRA UNO II thermocycler.

The samples (in triplicate) were analyzed on a 1% agarose gel, and product yield was densitometrically determined. Product yield in the samples without reverse transcriptase was set to 100%.

TABLE 1

Inhibitory effect of OMNISCRIPT RT on PCR

| | | \multicolumn{6}{c}{OMNISCRIPT RT (Units)} | | | | | |
|---|---|---|---|---|---|---|---|
| | | 0 | 0.2 | 0.5 | 1.0 | 2.0 | 5.0 |
| Template | $10^3$ | 100% | 84% | 47% | 25% | 14% | 2% |
| (copy number) | $10^2$ | 100% | 90% | 32% | 20% | 8% | 1% |

The results clearly demonstrate that the presence of even little amounts of reverse transcriptase dramatically reduced DNA replication efficiency when only a limiting amount of template DNA was present. Comparable experiments using genomic DNA as template confirmed the inhibiting effect of OMNISCRIPT RT on PCR, especially when minute amounts of template DNA were used.

EXAMPLE 2
Reduction of Reverse Transcriptase Inhibition of Nucleic Acid Amplification by Homopolymeric poly(A)

To demonstrate the discovery that the inhibitory effect of reverse transcriptase on DNA replication is relieved by the use of homopolymeric poly(A), increasing amounts of poly(A) (commercially obtained from Pharmacia) were added to samples containing various amounts of total RNA from HeLa cells. A 626 bp fragment of the β-actin mRNA from HeLa total RNA was selected as the RNA template for RT-PCR.

Reactions were conducted in a final volume of 50 μl. Two reaction mixtures comprised 50 mM KCl, 10 mM Tris-HCl, pH 8.3, 0.001% gelatine, 2.5 mM MgCl$_2$, 2 mM DTT, 400 μM each dNTP, 0.4 μM sense and antisense primers (SEQ ID NOs: 3 and 4, respectively), 5 Units HOTSTARTAQ DNA polymerase (QIAGEN), 0.5 Units OMNISCRIPT RT and 1 and 10 ng of HeLa total RNA, respectively. Reactions were performed in the presence of 0 ng, 100 ng, 200 ng and 400 ng of poly(A) homopolymer. Reverse transcription was done at 42° C. for 30 min. The PCR program consisted of an initial RT denaturation/HOTSTARTAQ activation step (15 min, 95° C.), 40 cycles (1 min, 94° C.; 1 min, 60° C., 1 min, 72° C.) and a final extension step (10 min, 72° C.). RT-PCR was per in an Eppendorf gradient cycler.

The samples (in duplicate) were analyzed on a 1% agarose gel. A clear improvement in efficiency and specificity upon addition of poly(A) was observed for both the 1 and 10 ng of total HeLa RNA samples. The yield of RT-PCR significantly increased with increasing amounts of poly(A). FIG. 1 shows the effect of poly(A) when using 1 ng of HeLa total RNA as template. The same effect was observed when 10 ng of total HeLa RNA were used as template (data not shown). The results demonstrate that the addition of poly(A) homopolymer reduces the inhibiting effect of OMNISCRIPT RT (QIAGEN) on HOTSTARTAQ DNA Polymerase (QIAGEN), thereby contributing to higher sensitivity and specificity in the one-step RT-PCR.

EXAMPLE 3
Reduction of Reverse Transcriptase Inhibition of Nucleic Acid Amplification by Other Homopolymeric Ribonucleic Acids The experiments described in Example 2 were replicated, using poly(U) and poly(C) in place of poly(A), to demonstrate that the reduction of the inhibitory effect of reverse transcriptase on DNA replication, due to the presence of a homopolymeric ribonucleic acid, is a characteristic common to homopolymeric ribonucleic acids generally.

The same 626 bp fragment of β-actin mRNA was selected as the template RNA. Reactions were conducted in a final volume of 50 μl. The reaction mixture comprised 50 mM KCl, 10 mM Tris-HCl, pH 8.3, 0.001% gelatine, 2.5 mM MgCl$_2$, 2 mM DTT, 400 μM each dNTP, 0.4 μM sense and antisense primers (SEQ ID NOs: 3 and 4, respectively), 5 Units HOTSTARTAQ DNA polymerase (QIAGEN), 0.5 Units OMNISCRIPT RT (QIAGEN) and 1 ng of HeLa total RNA. Reactions were performed in the presence of 0 ng, 100 ng, 200 ng and 400 ng of poly(U) (Pharmacia) and poly(C) (Pharmacia) homopolymer, respectively. Reverse transcription was done at 42° C. for 30 min. The PCR program consisted of an initial RT denaturation/HOTSTARTAQ activation step (15 min, 95° C.), 40 cycles (1 min, 94° C.; 1 min, 60° C., 1 min, 72° C.) and a final extension step (10 min, 72° C.). RT-PCR was performed in an Eppendorf gradient cycler.

Figure 2:
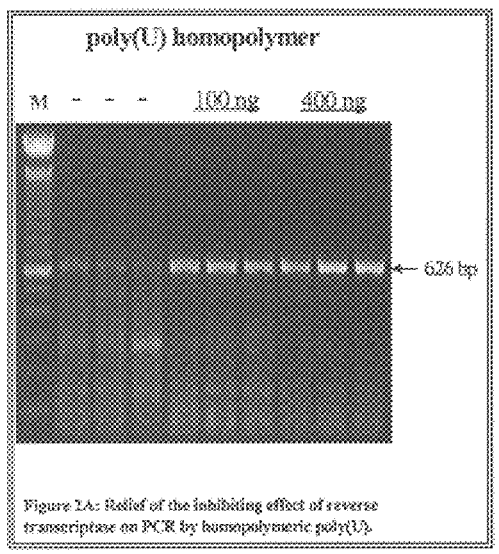
FIG. 2 is a photograph of an ethidium bromide (EtdBr)-stained 1% agarose gel, which depicts the reduction of reverse transcriptase inhibition of PCR by; 2a homopolymeric poly(U), and 2b homopolymeric poly(C). Lane 1 is a nucleic acid ladder, used as a gel reference marker. Lanes 2 and 3 are controls, which lack a homopolymeric nucleic acid. Lanes 4 and 5 show the nucleic acid products of an RT-PCR reaction in the presence of 100 ng of (2a) poly(U), or (2b) poly (C). Lanes 6 and 7 show the nucleic acid products of an RT-PCR reaction in the presence of 200 ng of (2a) poly(U), or (2b) poly (C). Lanes 8 and 9 show the nucleic acid products of an RT-PCR reaction in the presence of 400 ng of (2a) poly(U), or (2b) poly (C).
Figure 2:
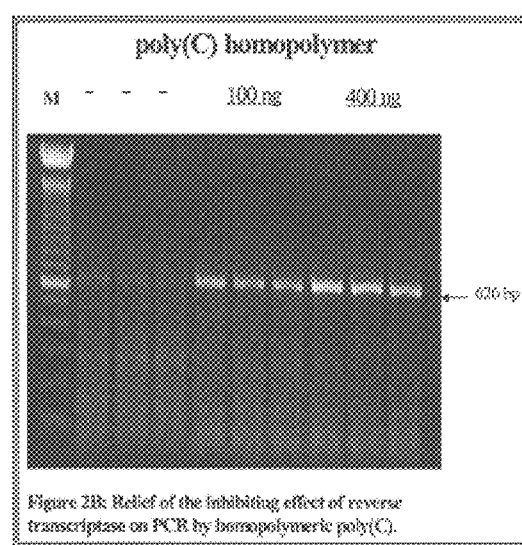

The samples (in triplicate) were analyzed on a 1% agarose gel. FIGS. 2a and 2b show the effect of poly(U) and poly(C), respectively, when using 1 ng of HeLa total RNA as template and 0 ng, 100 ng and 400 ng of the respective homopolymeric ribonucleic acid. The results of this series of experiments confirm that the addition of homopolymeric ribonucleic acids suppress or reduce the inhibitory effect of reverse transcriptase on DNA replication.

EXAMPLE 4
Reduction of Reverse Transcriptase Inhibition of Nucleic Acid Amplification by Homopolymeric Deoxyribonucleic Acids The experiments, as described in Examples 2 and 3, were repeated using a homopolymeric deoxyribonucleic acid (poly(dA)), to demonstrate that the reduction of the inhibitory effect of reverse transcriptase on DNA replication, is a feature common to homopolymeric nucleic acids generally.

The same 626 bp fragment of β-actin mRNA was selected as the template RNA. Reactions were conducted in a final volume of 50 μl. The reaction mixture comprised 50 mM KCl, 10 mM Tris-HCl, pH 8.3, 0.001% gelatine, 2.5 mM MgCl$_2$, 2 mM DTT, 400 μM each dNTP, 0.4 μM sense and antisense primers (SEQ ID NOs: 3 and 4 respectively), 5 Units HOTSTARTAQ DNA polymerase (QIAGEN), 0.5 Units OMNISCRIPT RT (QIAGEN) and 1 ng of HeLa total RNA. Reactions were performed in the presence of 0 ng, 100 ng, 200 ng and 400 ng of poly(dA) homopolymer (Pharmacia). Reverse transcription was done at 42° C. for 30 min. The PCR program consisted of an initial RT denaturation/HOTSTARTAQ activation step (15 min, 95° C.), 40 cycles (1 min, 94° C.; 1 min, 60° C., 1 min, 72° C.) and a final extension step (10 min, 72° C.). RT-PCR was performed in an Eppendorf gradient cycler.

Figure 3:
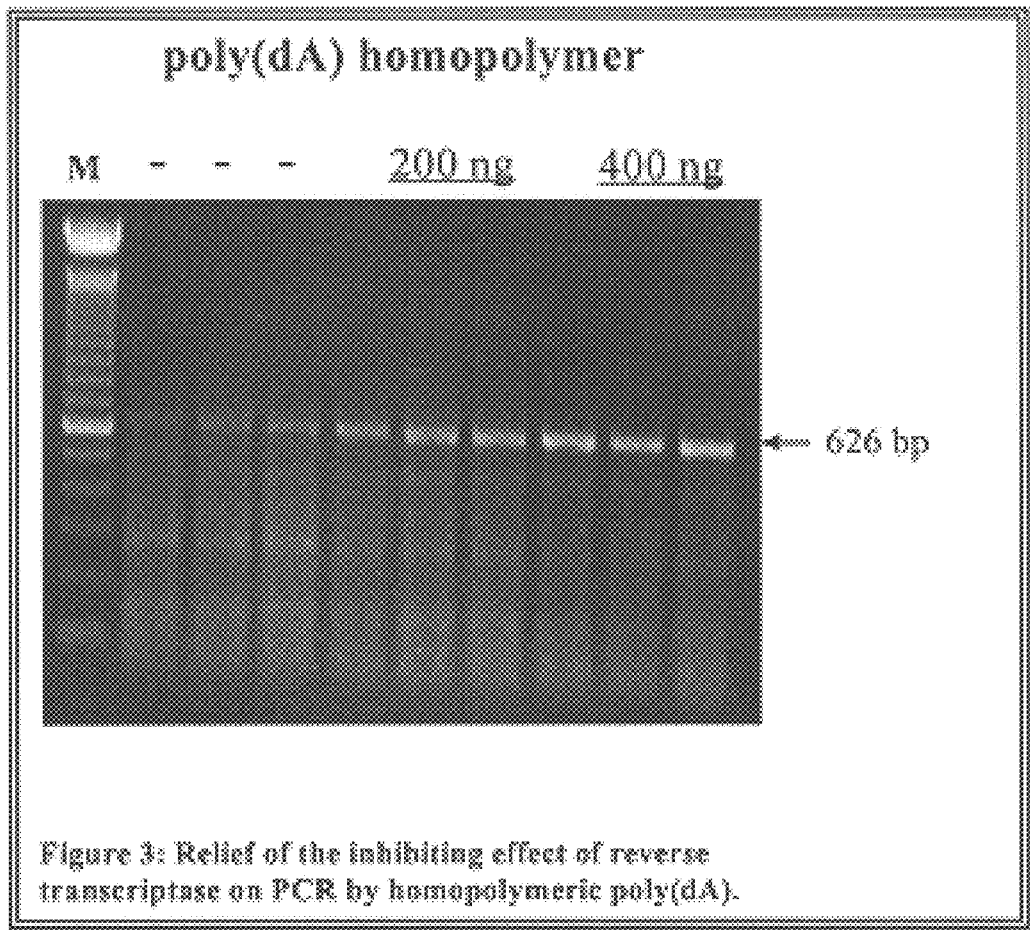
FIG. 3 is a photograph of an ethidium bromide (EtdBr)-stained 1% agarose gel, which depicts the reduction of reverse transcriptase inhibition of PCR by homopolymeric poly(dA). Lane 1 is a nucleic acid ladder, used as a gel reference marker. Lanes 2 through 4 are controls, which lack homopolymeric poly(dA). Lanes 5 through 7 show the nucleic acid products of an RT-PCR reaction in the presence of 200 ng of poly(dA). Lanes 8 through 10 show the nucleic acid products of an RT-PCR reaction in the presence of 400 ng of poly(A).

The samples (in triplicate) were analyzed on a 1% agarose gel. FIG. 3 illustrates the addition of poly(dA) substantially improves RT-PCR. These results confirm that the inhibitory effect of reverse transcriptase on DNA replication is reduced by addition of homopolymeric nucleic acids, generally (deoxyribonucleic acids as well as ribonucleic acids).

EXAMPLE 5
Reduction of Reverse Transcriptase Inhibition of Nucleic Acid Amplification by Homopolymeric Nucleic Acids Under Varying Reverse Transcriptase Conditions To demonstrate that the effectiveness of the present invention to reduce the inhibitory effect of reverse transcriptase on DNA replication is independent of the reverse transcriptase used, experiments of the earlier examples were repeated using a variety of enzymes that exhibit reverse transcriptase activity.

The same 626 bp fragment of β-actin mRNA was selected as the template RNA. Reactions were conducted in a final volume of 50 µl. The reaction mixture comprised 50 mM KCl, 10 mM Tris-HCl, pH 8.3, 0.001% gelatine, 2.5 mM $MgCl_2$, 2 mM DTT, 400 µM of each dNTP, 0.4 µM sense and antisense primers (SEQ ID NOs: 3 and 4 respectively), 5 Units HOTSTARTAQ DNA polymerase (QIAGEN), and 1 and 10 ng of HeLa total RNA, respectively. Three reverse transcriptases were tested. The reaction mixture contained either; 10 Units AMV-RT (Roche Molecular Biochemicals), 50 Units M-MLV-RT (Promega, recombinant), or 50 Units M-MLV, RNaseH -RT (Superscript II RT, LTI, recombinant). Reactions were performed in the presence of 0 ng, 100 ng, 200 ng and 400 ng of poly(A) homopolymer. Reverse transcription was done at 42° C. for 30 min. The PCR program consisted of an initial RT denaturation/ HOTSTARTAQ activation step (15 min, 95° C.), 40 cycles (1 min, 94° C.; 1 min, 60° C., 1 min, 72° C.) and a final extension step (10 min, 72° C.). RT-PCR was performed in a Biometra Uno II thermal cycler.

Figure 4:
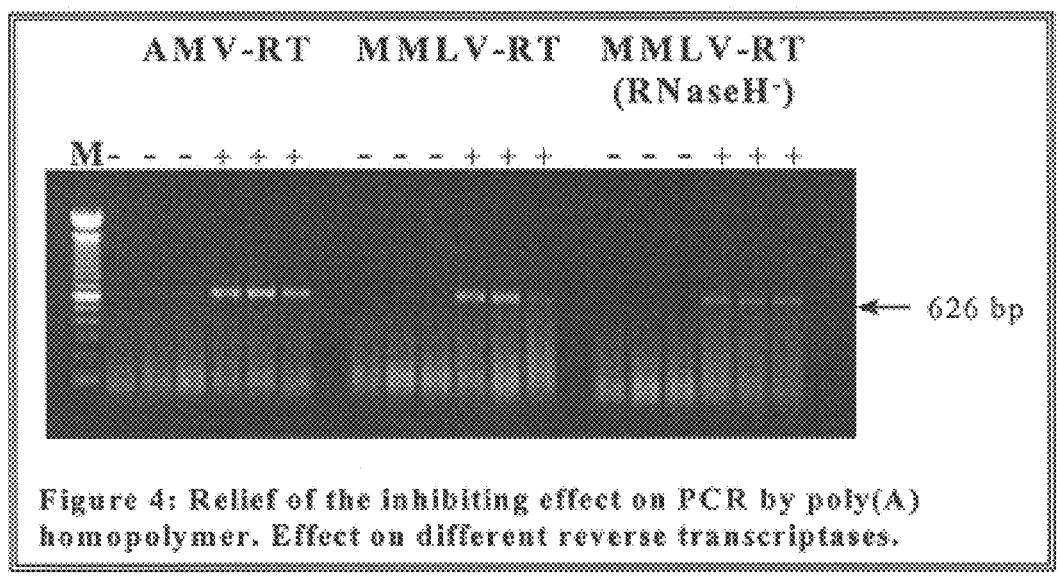
FIG. 4 is a photograph of an ethidium bromide (EtdBr)-stained 1% agarose gel, which depicts the reduction effects of homopolymeric poly(A) on PCR inhibition involving different reverse transcriptases. Lane 1 is a nucleic acid ladder, used as a gel reference marker. Lanes 2 through 4, 9 through 11, and 16 through 18 are controls, which lack homopolymeric poly(A). Lanes 5 through 7 show the nucleic acid products of an RT-PCR reaction using AMV-RT. Lanes 12 through 14 show the nucleic acid products of an RT-PCR reaction using MMLV-RT. Lanes 19 through 21 show the nucleic acid products of an RT-PCR reaction using MMLV-RT RNase H-. (Lanes 8 and 15 are unused as spacers.)

A clear increase in sensitivity (i.e., reduced inhibition of PCR in the one-step RT-PCR) was observed for all three reverse transcriptases tested. FIG. 4 summarizes the results (in triplicate) with β-actin as the template in the absence (–) or presence of 400 ng poly(A) homopolymer (+). For AMV-RT and MMLV-RT, results with 1 ng of total RNA as template are shown. For M-MLV, RNaseH RT, the results obtained with 10 ng template RNA are shown.

These results confirm the effectiveness of the present invention to reduce the inhibitory effect of reverse transcriptase on DNA replication, independent of the reverse transcriptase used in the reaction mixture. The present invention can be used as a general optimization component of RT-PCR, irrespective of the reverse transcriptase used.

EXAMPLE 6
Reduction of Reverse Transcriptase Inhibition of Nucleic Acid Amplification by Homopolymeric Nucleic Acids Under Varying DNA Polymerase, Buffer and Salt Conditions To further demonstrate the general utility of the present invention to reduce the inhibitory effect of reverse transcriptase on DNA replication in a variety of reaction mixtures, trials were conducted employing different DNA polymerases, buffering agents and salt solutions.

Two DNA polymerases were tested; unmodified, recombinant Taq DNA-Polymerase (AmpliTaq, Perkin Elmer), and recombinant Pfu DNA polymerase (Stratagene). One trial series employed 5 Units AMPLITAQ DNA Polymerase in a reaction mixture comprising 50 mM KCl, 10 mM Tris-HCl, pH 8.3, 0.001% gelatine, 2.5 mM $MgCl_2$, 400 µM of each dNTP, and 1 ng of HeLa total RNA. The second trial series employed 5 units Pfu DNA polymerase in a reaction mixture comprising 20 mM Tris-HCl, pH 8.8, 10 mM KCl, 10 mM $(NH_4)_2SO_4$, 2 mM $MgSO_4$, 0.1% TRITON X-100 non-ionic detergent, 0.1 mg/ml BSA, 200 µM of each dNTP, and 1 ng or 100 ng of HeLa total RNA. All reaction mixtures contained 2 mM DTT, 0.4 µM sense and antisense primers (SEQ ID NOs: 3 and 4, respectively), and 0.5 units OMNISCRIPT RT. Reactions were performed in a final volume of 50 µl.

Reactions were performed in the presence of 0 ng, 100 ng, 200 ng and 400 ng of poly(A) homopolymer. Reverse transcription was done at 42° C. for 30 min. The PCR program consisted of an initial RT denaturation step (5 min, 94° C.), 40 cycles (1 min, 94° C.; 1 min, 60° C., 1 min, 72° C.) and a final extension step (10 min, 72° C.). RT-PCR was performed in a Biometra Uno II thermal cycler.

Figure 5:
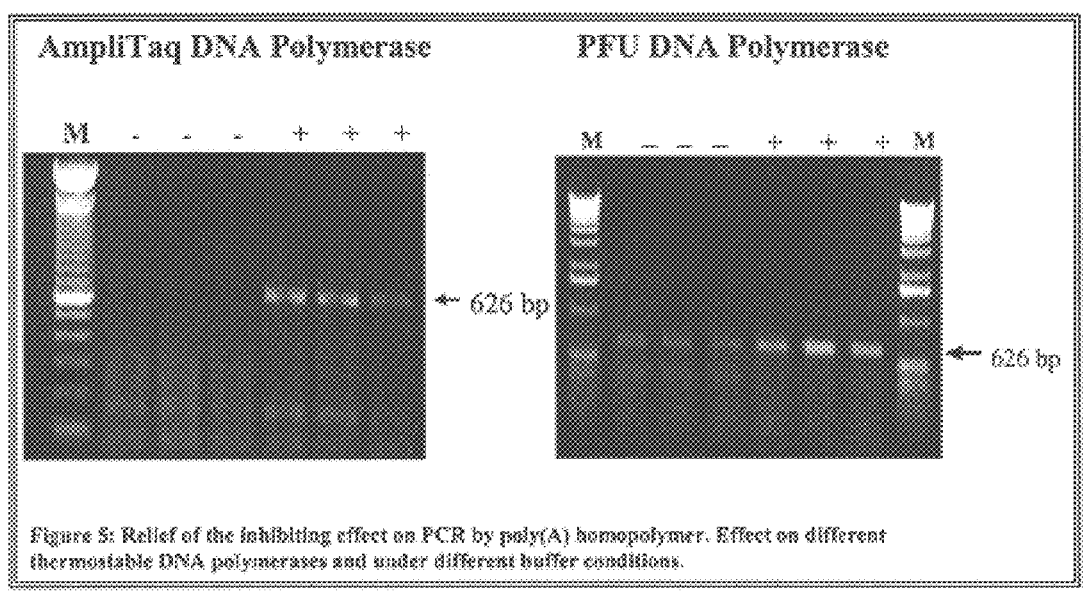
FIG. 5 is a photograph of an ethidium bromide (EtdBr)-stained 1% agarose gel, which depicts the reduction effects of homopolymeric poly(A) on different DNA polymerases and under different buffer and salt conditions.

Results confirm improved nucleic acid amplification occurred in the presence of the homopolymeric nucleic acid, regardless of DNA polymerase, buffering agent or salt solution used in the final reaction mixture. FIGS. 5a and 5b depict the results using 1 ng of total HeLa RNA in the absence (–), or presence (+) of 400 ng poly(A). The inhibition-relieving effect of homopolymeric nucleic acids in coupled RT-PCR is not limited to a particular thermostable DNA polymerase, a particular buffering agent or salt solution. It has, therefore, been demonstrated that the present invention is useful under varying ionic conditions, different pH values, and can be applied to various DNA polymerases.

EXAMPLE 7
Reduction of Reverse Transcriptase Inhibition of Nucleic Acid Amplification by Homopolymeric Nucleic Acids On Different Target Ribonucleic Acids To demonstrate that the effectiveness of the present invention to reduce the inhibitory effect of reverse transcriptase on DNA replication is independent of the target RNA sought and the oligonucleotide primers used, trials were conducted seeking to reverse transcribe and replicate a different gene fragment. For these trials a 690 bp fragment of the (α-catenin MRNA from total HeLa RNA was selected as the RNA template for RT-PCR.

Reactions were conducted in a final volume of 50 µl. The reaction mixture comprised 50 mM KCl, 10 mM Tris-HCl, pH 8.3, 0.001% gelatine, 2.5 mM $MgCl_2$, 2 mM DTT, 400 µM of each dNTP, 0.4 µM sense and antisense primers (SEQ ID NOs: 5 and 6, respectively), 5 Units HOTSTARTAQ DNA polymerase (QIAGEN), 0.5 Units OMNISCRIPT RT and 5 ng of total HeLa RNA. Reactions were performed in the presence of either 0 ng, or 500 ng of poly(A) homopolymer. Reverse transcription was done at 42° C. for 30 min. The PCR program consisted of an initial RT denaturation/ HOTSTARTAQ activation step (15 min, 95° C.), 40 cycles (1 min, 94° C.; 1 min, 50° C., 1 min, 72° C.) and a final extension step (10 min, 72° C.). RT-PCR was performed in an MJR PTC 200 thermal cycler.

The samples (in triplicate) were analyzed on a 1% agarose gel. A clear improvement in efficiency and specificity upon addition of poly(A) was observed for reverse transcription and amplification of the a-catenin template from 5 ng of HeLa total RNA (see FIG. 6). The results confirm the inhibition-relieving effect of homopolymeric nucleic acids in coupled RT-PCR is specific to a particular template RNA or use of a particular oligonucleotide primer.

The results demonstrate that the addition of poly(A) homopolymer reduces the inhibiting effect of OMNISCRIPT RT (QIAGEN) on HOTSTARTAQ DNA Polymerase (QIAGEN), thereby contributing to higher sensitivity and specificity in the one-step RT-PCR.

EXAMPLE 8
Reduction of Reverse Transcriptase Inhibition of Nucleic Acid Amplification by Homopolymeric Nucleic Acids Compared to Other Nucleic Acids The previous examples have shown, conclusively, the positive effect of homopolymeric nucleic acids in reducing the inhibitory effect of reverse transcriptase on DNA replication independent of the reverse transcriptase, DNA polymerase, oligonucleotide primer, RNA template, buffering agent, or salt solution used in the reaction mixture.

To demonstrate the unique benefits of the present invention to reduce the inhibitory effect of reverse transcriptase on DNA replication, simultaneous trials were conducted comparing the effect on homopolymeneric nucleic acids to other nucleic acids, specifically non-homologous RNA molecules.

The 690 bp fragment of the α-catenin MnRNA was selected as the RNA template. Reactions were conducted in a final volume of 50 μl. The reaction mixture comprised 50 mM KCl, 10 mM Tris-HCl, pH 8.3, 0.001% gelatine, 2.5 mM MgCl$_2$, 2 mM DTT, 400 μM of each dNTP, 0.4 μM sense and antisense primers (SEQ ID NOs: 5 and 6, respectively), 5 Units HOTSTARTAQ DNA polymerase (QIAGEN), 0.5 Units OMNISCRIPT RT (QIAGEN), and 5 ng of HeLa total RNA.

The trial series consisted of reaction mixtures containing either no additional nucleic acid, 500 ng of poly(A) (Pharmacia), 500 ng tRNA (Sigma), or 500 ng E. coli 16S, 23 S rRNA (Roche Molecular Biochemicals). Reverse transcription was done at 42° C. for 30 min. The PCR program consisted of an initial RT denaturation/HOTSTARTAQ activation step (15 min, 95° C.), 40 cycles (1 min, 94° C.; 1 min, 50° C., 1 min, 72° C.) and a final extension step (10 min, 72° C.). RT-PCR was performed in an MJR PTC 200 thermal cycler.

Figure 6:
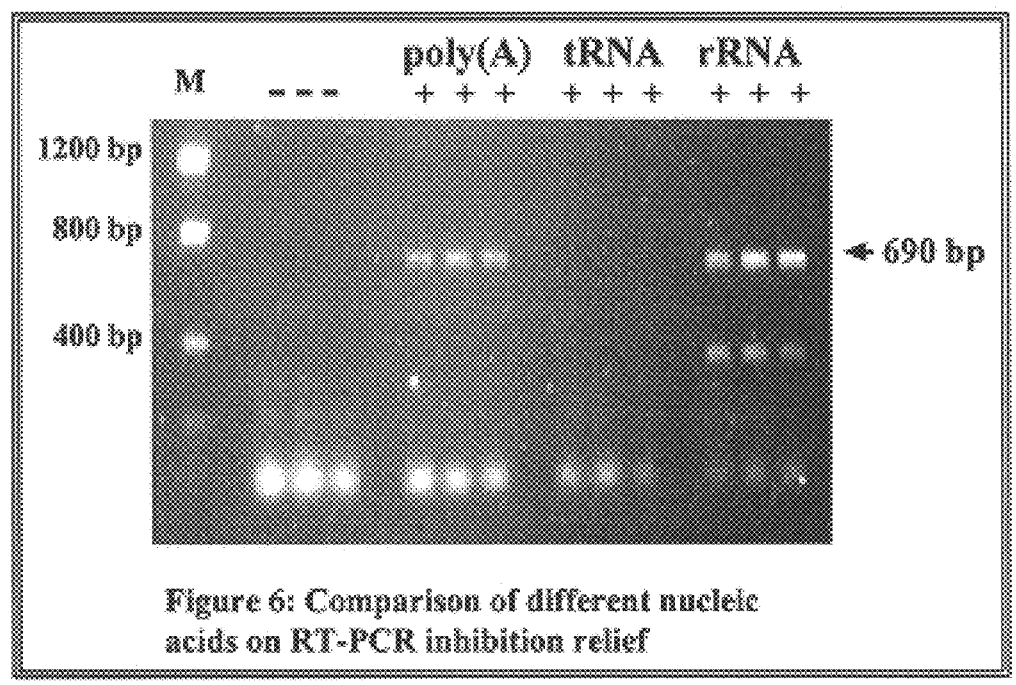
FIG. 6 is a photograph of an ethidium bromide (EtdBr)-stained 1% agarose gel, which depicts the reduction of reverse transcriptase inhibition of PCR by a homopolymeric nucleic acid compared to that of tRNA and rRNA. Lane 1 is a nucleic acid ladder, used as a gel reference marker. Lanes 3 through 5 are controls, which lack any nucleic acid additive to the standard RT-PCR reaction mixture. Lanes 7 through 9 show the nucleic acid products of an RT-PCR reaction in the presence of homopolymeric poly(A). Lanes 11 through 13 show the nucleic acid products of an RT-PCR reaction in the presence of tRNA. Lanes 15 through 17 show the nucleic acid products of an RT-PCR reaction in the presence of rRNA. (Lanes 2, 6, 10, and 14 are unused as spacers.)

FIG. 6 shows the comparative results of RT-PCR in the absence (−) or presence (+) of additional nucleic acids. When, except for template RNA, no further RNA was present in the reaction mixture, hardly any DNA product could be detected. Similar negative results were obtained when 500 ng tRNA was added to the reaction mixture, thereby corroborating the observations of Chandler et al. (1998) who could not confirm the positive effect of tRNA in one-step RT-PCR postulated by Sellner et al. (1992). The addition of 500 ng rRNA to the reaction led to the amplification of the desired nucleic acid product. A second unspecific band in the size range of 400 bp also appeared, however. This result clearly illustrates the clear disadvantages of using rRNA as inhibition-relieving agent based on theoretical considerations that such molecules serve as potential targets for mispriming. Only the utilization of the homopolymeric nucleic acid resulted in a clear improvement of RT-PCR, confirming the superiority of the compositions and methods of the present invention to reduce the inhibitory effect of reverse transcriptase on DNA replication.

The present invention incorporates by reference in their entirety techniques well known in the field of molecular biology. These techniques include, but are not limited to, techniques described in the following publications:

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Sambrook, J. et al. eds., *Molecular Cloning: A Laboratory Manual* (2d Ed. 1989) Cold Spring Harbor Laboratory Press, N.Y. Vols. 1–3. (ISBN 0-87969-309-6).

Winnacker, E. L. *From Genes To Clones: Introduction To Gene Technology* (1987) VCH Publishers, N.Y. (translated by Horst Ibelgaufts). 634 pp. (ISBN 0-89573-614-4).

References

Chadwick et al. Comparison of three RNA amplification methods as sources of DNA for sequencing. *BioTechniques* 25(5):818–822 (Nov. 1998).

Chandler et al. Reverse transcriptase (RT) inhibition of PCR at low concentrations of template and its implications for quantitative RT-PCR. *Appl. and Environm. Microbiol.* 64(2):669–677 (Feb. 1998).

Compton, J. Nucleic acid sequence-based amplification. *Nature* 350:91–92 (1991).

Cusi et al. Comparison of M-MLV reverse transcriptase and Tth polymerase activity in RT-PCR of samples with low virus burden. *BioTechniques* 17:1034–1036 (1994).

Guatelli et al. Isothermal, in vitro amplification of nucleic acids by a multienzyme reaction modeled after retroviral replication. *PNAS USA* 87:1874–1878 (1990).

Juhasz et al. Sensitivity of tyrosinase mRNA detection by RT-PCR: rTth DNA polymerase vs. MMLV-RT and Amplitaq® polymerase. *BioTechniques* 20:592–600 (1996).

Mallet et al. Continuous RT-PCR using AMV-RT and Taq DNA polymerase: characterization and comparison to uncoupled procedures. *BioTechniques* 18:678–687 (1995).

Myers and Gelfand. Reverse transcription and DNA amplification by a *Thermus thermophilus* DNA polymerase. *Biochemistry* 30:7661–7666 (1991).

Saiki et al. Enzymatic amplification of beta-globin genomic sequences and restriction site analysis for diagnosis of sickle cell anaemia. *Science* 230:1350–1354 (1985).

Sellner and Turbett. Comparison of three RT-PCR methods. *BioTechniques* 25(2):230–234 (Aug. 1998).

Sellner et al. Reverse transcriptase inhibits Taq polymerase activity. *Nucl. Acids Res.* 20(7):1487–1490 (Apr. 11, 1992).

Sellner, et al. A one-tube, one manipulation RT-PCR reaction for detection of Ross River virus. *J. Virol. Methods* 40:255–264 (1992).

Sooknanan et al. Fidelity of nucleic acid amplification with avian myeloblastosis virus reverse transcriptase and T7 RNA polymerase. *BioTechniques* 17:1077–1085 (1994).

Xu, et al. The application of polymerase chain reaction to the detection of rotaviruses in faeces. *J. Virol. Methods* 27:29–38 (1990).

Young et al. Detection of hepatitis C virus RNA by a combined reverse transcription-polymerase chain reaction assay. *J. Clin. Microbiol.* 31:882–886 (1993).

Each of the publications mentioned herein is incorporated by reference.

We claim:

1. In a method for generating a nucleic acid from an RNA template comprising the steps:
   a) adding said RNA template to a reaction mixture, said reaction mixture comprising at least one reverse transcriptase and at least one nucleic acid polymerase, or derivatives thereof; and
   b) incubating said reaction mixture under conditions sufficient to allow polymerization of a nucleic acid molecule complementary to a portion of said RNA template,
wherein the improvement comprises a reaction mixture further comprising a homopolymeric oligonucleotide at least 50 bases in length.

2. The method of claim 1, wherein said reverse transcriptase is selected from the group consisting of: AMV-RT, M-MLV-RT, HIV-RT, EIAV-RT, RAV2-RT, *C. hydrogenoformans* DNA Polymerase, SUPERSCRIPT I (a variant reverse transcriptase isolated from Murine Leukemia Virus), and SUPERSCRIPT II (a variant reverse transcriptase isolated from Murine Leukemia Virus).

3. The method of claim 1, wherein said reaction mixture further comprises a nucleic acid primer.

4. The method of claim 1, wherein said DNA molecule complementary to a portion of said RNA template is amplified by a process of DNA replication.

5. The method of claim 3, wherein said primer is complementary to a portion of said RNA template.

6. The method of claim 4, wherein said process of DNA replication comprises a polymerase chain reaction (PCR).

7. The method of claim 4, wherein the combined reactions of DNA generation and amplification occurs in a coupled reaction mixture.

8. The method of claim 7, wherein the reaction proceeds between about 23° C. to about 100° C.

9. The method of claim 8, wherein reverse transcription occurs between about 37° C. to about 70° C. and said PCR amplification occurs between about 60° C. to about 95° C.

10. The method of claim 9, wherein said PCR amplification comprises at least 25 cycles of denaturation, annealization, and polymerization.

11. The method of claim 10, wherein said reverse transcription occurs between about 37° C. to about 60° C., denaturation occurs at about 94° C., annealization occurs at about 60° C., and polymerization occurs at about 72° C.

12. In a method for generating a nucleic acid from an RNA template comprising the steps:
   a) adding said RNA template to a reaction mixture, said reaction mixture comprising at least one reverse transcriptase, at least one nucleic acid polymerase, and one or more ribonucleotide triphosphate or derivatives thereof; and
   b) incubating said reaction mixture under conditions sufficient to allow polymerization of a nucleic acid molecule complementary to a portion of said RNA template,
wherein the improvement comprises a reaction mixture further comprising a homopolymeric oligonucleotide at least 50 bases in length.

13. The method of claim 12 wherein said nucleic acid is DNA, said polymerase is DNA polymerase, and said ribonucleic acid triphosphate derivative is selected from the group consisting of; dATP, dCTP, dGTP, dTTP, dITP, dUTP, α-thio-dNTPs, biotin-dUTP, fluorescein-dUTP, and digoxigenin-dUTP.

14. The method of claim 12, wherein said homopolymeric oligonucleotide is a homopolymeric ribonucleic acid.

15. The method of claim 12, wherein said homopolymeric oligonucleotide is a homopolymeric deoxyribonucleic acid.

16. The method of claim 13, wherein said DNA polymerase is a thermostable polymerase.

17. The method of claim 14, wherein said homopolymeric ribonucleic acid is selected from the group consisting of; homopolymeric poly(A), homopolymeric poly(U), homopolymeric poly(C), and homopolymeric poly(G).

18. The method of claim 15, wherein said homopolymeric deoxyribonucleic acid is selected from the group consisting of; homopolymeric poly(dA), homopolymeric poly(dI), homopolymeric poly(dC), homopolymeric poly(dG), and homopolymeric poly(dT).

19. The method of claim 16, wherein said DNA polymerase is selected from the group consisting of; Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENTM (a variant DNA polymerase isolated from *Thermococcus litoralis*), and DEEPVENT® (a variant DNA polymerase isolated from Pyrococcus sp.).

20. In a composition suitable for reverse transcription of RNA, comprising at least one member of the group consisting of: a reverse transcriptase, a DNA polymerase, one or more oligonucleotide primers, any one or more nucleotides or derivatives thereof, a buffering agent, a salt, and additives useful in RT-PCR, wherein the improvement comprises a homopolymeric oligonucleotide at least 50 bases in length.

21. The composition of claim 20, wherein said homopolymeric oligonucleotide is a homopolymeric ribonucleic acid.

22. The composition of claim 20, wherein said homopolymeric oligonucleotide is a homopolymeric deoxyribonucleic acid.

23. The composition of claim 20, wherein the composition contains at least 10 ng of homopolymer.

24. The composition of claim 20 further comprising a reverse transcriptase.

25. The composition of claim 20 further comprising a DNA polymerase.

26. The composition of claim 20 further comprising one or more oligonucleotide primers.

27. The composition of claim 20 further comprising a buffering agent.

28. The composition of claim 20 further comprising a salt solution.

29. The composition of claim 20 further comprising an additive useful in RT-PCR.

30. The composition of claim 20 further comprising one or more nucleotides.

31. The composition of claim 20, wherein said homopolymeric oligonucleotide is at least 100 bases in length.

32. The composition of claim 21, wherein said homopolymeric ribonucleic acid is selected from the group consisting of, homopolymeric poly(A), homopolymeric poly(U), homopolymeric poly(C), and homopolymeric poly(G).

33. The composition of claim 22, wherein said homopolymeric deoxyribonucleic acid is selected from the group consisting of; homopolymeric poly(dA), homopolymeric poly(dI), homopolymeric poly(dC), homopolymeric poly(dG), and homopolymeric poly(dT).

34. The composition of claim 23, wherein the composition contains between 10 to 2000 ng of homopolymer.

35. The composition of claim 24, wherein said reverse transcriptase is selected from the group consisting of: AMV-RT, M-MLV-RT, HIV-RT, EIAV-RT, RAV2-RT, *C. hydrogenoformans* DNA Polymerase, SUPERSCRIPT I (a variant reverse transcriptase isolated from Murine Leukemia Virus), and SUPERSCRIPT II (a variant reverse transcriptase isolated from Murine Leukemia Virus).

36. The composition of claim 25, wherein said DNA polymerase is selected from the group consisting of; Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT® (a variant DNA polymerase isolated from *Thermococcus litoralis*), and DEEPVENT® (a variant DNA polymerase isolated from Pyrococcus sp.).

37. The composition of claim 26, wherein said primer is selected from the group consisting of; random primers, homopolymers, and primers specific to a target RNA template.

38. The composition of claim 27, wherein said buffering agent is selected from the group consisting of; TRIS, TRICINE, BIS-TRICINE, HEPES, MOPS, TES, TAPS, PIPES, and CAPS.

39. The composition of claim 28, wherein said salt solution is selected from the group consisting of; potassium chloride, potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

40. The composition of claim 29, wherein said additive useful in RT-PCR is selected from the group consisting of: DMSO, glycerol, formamide, betain, tetramethylammonium chloride, PEG, non-ionic surfacant, ectoine, polyols, *E. coli* SSB protein, Phage T4 gene 32 protein, and BSA.

41. The composition of claim 30, wherein said nucleotide is a deoxyphosphonucleotide or derivative thereof.

42. The composition of claim 41, wherein said deoxyphosphonucleotide is selected from the group consisting of; DATP, dCTP, dGTP, dTTP, dITP, dUTP, ($\alpha$-thio-dNTPs, biotin-dUTP, fluorescein-dUTP, and digoxigenin-dUTP.

43. The composition of claim 34, wherein the composition contains between 100 to 1000 ng of homopolymer.

44. The composition of claim 43, wherein the composition contains between 200 to 600 ng of homopolymer.

45. The composition of claim 20, wherein said homopolymeric oligonucleotide is less than 5000 bases in length.

* * * * *